(12) United States Patent
Youker

(10) Patent No.: US 8,406,882 B2
(45) Date of Patent: Mar. 26, 2013

(54) IMPLANTABLE PULSE GENERATOR WITH A STACKED BATTERY AND CAPACITOR

(75) Inventor: Nick A. Youker, River Falls, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/285,111

(22) Filed: Oct. 31, 2011

(65) Prior Publication Data

US 2012/0045668 A1 Feb. 23, 2012

Related U.S. Application Data

(60) Continuation of application No. 13/041,651, filed on Mar. 7, 2011, now Pat. No. 8,055,346, which is a division of application No. 12/178,876, filed on Jul. 24, 2008, now Pat. No. 7,917,207, which is a continuation of application No. 11/117,952, filed on Apr. 29, 2005, now abandoned.

(51) Int. Cl.
  *A61N 1/375* (2006.01)
(52) U.S. Cl. ........................................... 607/36
(58) Field of Classification Search .............. 607/34, 607/2, 36–37
See application file for complete search history.

(56) References Cited

U.S. PATENT DOCUMENTS

| | | |
|---|---|---|
| 3,389,311 A | 6/1968 | Rayno |
| 3,803,457 A | 4/1974 | Yamamoto |
| 3,993,508 A | 11/1976 | Erlichman |
| 4,113,921 A | 9/1978 | Goldstein et al. |
| 4,243,042 A | 1/1981 | Ware |
| 4,254,775 A | 3/1981 | Langer |
| 4,315,974 A | 2/1982 | Athearn |
| 4,659,636 A | 4/1987 | Suzuki et al. |
| 5,131,388 A | 7/1992 | Pless et al. |
| 5,173,375 A | 12/1992 | Cretzmeyer et al. |
| 5,367,437 A | 11/1994 | Anderson |
| 5,370,663 A | 12/1994 | Lin |
| 5,370,669 A | 12/1994 | Daglow et al. |
| 5,422,200 A | 6/1995 | Hope et al. |
| 5,456,698 A | 10/1995 | Byland et al. |
| 5,470,676 A | 11/1995 | Nakano |
| 5,522,851 A | 6/1996 | Fayram |
| 5,527,346 A | 6/1996 | Kroll |
| 5,591,211 A | 1/1997 | Meltzer |
| 5,640,756 A | 6/1997 | Brown et al. |

(Continued)

FOREIGN PATENT DOCUMENTS

| | | |
|---|---|---|
| EP | 0224733 A1 | 6/1987 |
| EP | 0471661 A1 | 2/1992 |

(Continued)

OTHER PUBLICATIONS

"U.S. Appl. No. 11/467,808, Response filed Sep. 27, 2011 to Final Office Action mailed Jun. 27, 2011", 15 pgs.

(Continued)

*Primary Examiner* — Scott Getzow
*Assistant Examiner* — Amanda Patton
(74) *Attorney, Agent, or Firm* — Schwegman Lundberg & Woessner, P.A.

(57) ABSTRACT

One example includes a configurable power source system for an implantable device having a predetermined power requirement, the system comprising a housing for a battery and a capacitor, the housing including a distance D between a first internal face and a second internal face, the housing adapted to fit within dimensions of the implantable device, a plurality of batteries of different thicknesses, each battery adapted to fit within a perimeter of the housing, a plurality of capacitors of different thicknesses, each capacitor adapted to fit within the housing and adjacent the battery and a pick and place system adapted to assemble a selected battery from the plurality of batteries and a selected capacitor from the plurality of capacitors with the housing to form a configurable power source at least meeting the predetermined power requirement for the implantable device.

20 Claims, 4 Drawing Sheets

U.S. PATENT DOCUMENTS

| | | |
|---|---|---|
| 5,658,319 A | 8/1997 | Kroll |
| 5,691,079 A | 11/1997 | Daugaard |
| 5,697,953 A | 12/1997 | Kroll et al. |
| 5,749,911 A | 5/1998 | Westlund |
| 5,776,632 A | 7/1998 | Honegger |
| 5,800,857 A | 9/1998 | Ahmad et al. |
| 5,801,917 A | 9/1998 | Elias |
| 5,814,082 A | 9/1998 | Fayram et al. |
| 5,882,362 A | 3/1999 | Muffoletto et al. |
| 5,896,647 A | 4/1999 | Shkuratoff |
| 5,930,109 A | 7/1999 | Fishler |
| 5,954,751 A | 9/1999 | Chen et al. |
| 5,963,418 A | 10/1999 | Greenwood, Jr. et al. |
| 6,006,133 A | 12/1999 | Lessar et al. |
| 6,009,348 A | 12/1999 | Rorvick et al. |
| 6,010,317 A | 1/2000 | Maget et al. |
| 6,032,075 A | 2/2000 | Pignato et al. |
| 6,040,082 A | 3/2000 | Haas et al. |
| 6,042,624 A | 3/2000 | Breyen et al. |
| 6,118,651 A | 9/2000 | Mehrotra et al. |
| 6,118,652 A | 9/2000 | Casby et al. |
| 6,184,160 B1 | 2/2001 | Yan et al. |
| 6,185,452 B1 | 2/2001 | Schulman et al. |
| 6,212,063 B1 | 4/2001 | Johnson et al. |
| 6,275,729 B1 | 8/2001 | O'Phelan et al. |
| 6,283,985 B1 | 9/2001 | Harguth et al. |
| 6,297,943 B1 | 10/2001 | Carson |
| 6,321,114 B1 | 11/2001 | Nutzman et al. |
| 6,330,925 B1 | 12/2001 | Ovshinsky et al. |
| 6,371,997 B1 | 4/2002 | Chang et al. |
| 6,388,284 B2 | 5/2002 | Rhodes et al. |
| 6,388,866 B1 | 5/2002 | Rorvick et al. |
| 6,404,619 B1 | 6/2002 | Marshall et al. |
| 6,445,948 B1 | 9/2002 | Somdahl et al. |
| 6,459,566 B1 | 10/2002 | Casby et al. |
| 6,498,951 B1 | 12/2002 | Larson et al. |
| 6,522,525 B1 | 2/2003 | O'Phelan et al. |
| 6,556,863 B1 | 4/2003 | O'Phelan et al. |
| 6,571,126 B1 | 5/2003 | O'Phelan et al. |
| 6,632,720 B2 | 10/2003 | Barr et al. |
| 6,674,634 B2 | 1/2004 | O'Phelan et al. |
| 6,678,559 B1 | 1/2004 | Breyen et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,721,602 B2 | 4/2004 | Engmark et al. |
| 6,763,265 B2 | 7/2004 | O'Phelan et al. |
| 6,799,072 B2 | 9/2004 | Ries et al. |
| 6,833,987 B1 | 12/2004 | O'Phelan |
| 6,881,516 B2 | 4/2005 | Aamodt et al. |
| 6,885,887 B2 | 4/2005 | O'Phelan et al. |
| 6,957,103 B2 | 10/2005 | Schmidt et al. |
| 6,963,482 B2 | 11/2005 | Breyen et al. |
| 6,985,351 B2 | 1/2006 | O'Phelan et al. |
| 6,990,375 B2 | 1/2006 | Kloss et al. |
| 6,999,304 B2 | 2/2006 | Schmidt et al. |
| 7,072,713 B2 | 7/2006 | O'Phelan et al. |
| 7,079,897 B2 | 7/2006 | Sun et al. |
| 7,089,982 B2 | 8/2006 | Barr et al. |
| 7,107,099 B1 | 9/2006 | O'Phelan et al. |
| 7,120,008 B2 | 10/2006 | Sherwood |
| 7,154,739 B2 | 12/2006 | O'Phelan |
| 7,157,671 B2 | 1/2007 | O'Phelan et al. |
| 7,177,692 B2 | 2/2007 | O'Phelan et al. |
| 7,180,727 B2 | 2/2007 | Poplett |
| 7,190,569 B2 | 3/2007 | O'Phelan et al. |
| 7,190,570 B2 | 3/2007 | Schmidt et al. |
| 7,206,191 B2 | 4/2007 | Sherwood et al. |
| 7,221,556 B2 | 5/2007 | Schmidt et al. |
| 7,224,575 B2 | 5/2007 | Sherwood |
| 7,347,880 B2 | 3/2008 | O'Phelan et al. |
| 7,355,841 B1 | 4/2008 | Schmidt et al. |
| 7,365,960 B2 | 4/2008 | O'Phelan et al. |
| 7,419,873 B2 | 9/2008 | Doffing et al. |
| 7,443,652 B2 | 10/2008 | Sherwood |
| 7,456,077 B2 | 11/2008 | Sherwood et al. |
| 7,479,349 B2 | 1/2009 | O'Phelan et al. |
| 7,554,791 B2 | 6/2009 | Sherwood et al. |
| 7,576,973 B2 | 8/2009 | Schmidt et al. |
| 7,768,772 B2 | 8/2010 | Doffing et al. |
| 7,917,207 B2 | 3/2011 | Youker |
| 8,055,346 B2 | 11/2011 | Youker |
| 2002/0106554 A1 | 8/2002 | Nemoto et al. |
| 2002/0142216 A1 | 10/2002 | Skoumpris |
| 2002/0161404 A1 | 10/2002 | Schmidt |
| 2003/0072124 A1 | 4/2003 | O'Phelan et al. |
| 2003/0165744 A1 | 9/2003 | Schubert et al. |
| 2003/0195568 A1 | 10/2003 | O'Phelan et al. |
| 2003/0204216 A1 | 10/2003 | Ries et al. |
| 2004/0019268 A1 | 1/2004 | Schmidt et al. |
| 2004/0039421 A1 | 2/2004 | O'Phelan et al. |
| 2004/0114311 A1 | 6/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2004/0220627 A1 | 11/2004 | Crespi et al. |
| 2004/0230250 A1 | 11/2004 | Neumann et al. |
| 2005/0010253 A1 | 1/2005 | O'Phelan et al. |
| 2005/0017888 A1 | 1/2005 | Sherwood et al. |
| 2005/0041366 A1 | 2/2005 | Breven et al. |
| 2005/0052825 A1 | 3/2005 | O'Phelan |
| 2005/0154423 A1 | 7/2005 | Goedeke et al. |
| 2005/0221171 A1 | 10/2005 | Haasl et al. |
| 2005/0264979 A1 | 12/2005 | Breyen et al. |
| 2006/0009808 A1 | 1/2006 | Schmidt et al. |
| 2006/0012942 A1 | 1/2006 | Poplett |
| 2006/0023400 A1 | 2/2006 | Sherwood |
| 2006/0107506 A1 | 5/2006 | Doffing et al. |
| 2006/0152887 A1 | 7/2006 | Schmidt et al. |
| 2006/0174463 A1 | 8/2006 | O'Phelan et al. |
| 2006/0179626 A1 | 8/2006 | Poplett |
| 2006/0247715 A1 | 11/2006 | Youker |
| 2006/0257726 A1 | 11/2006 | Kelley et al. |
| 2007/0118182 A1 | 5/2007 | O'Phelan |
| 2008/0030928 A1 | 2/2008 | Schmidt et al. |
| 2008/0091246 A1 | 4/2008 | Carey et al. |
| 2008/0154319 A1 | 6/2008 | O'Phelan et al. |
| 2009/0025207 A1 | 1/2009 | Youker |
| 2009/0059472 A1 | 3/2009 | Sherwood et al. |
| 2009/0123825 A1 | 5/2009 | O'Phelan et al. |
| 2010/0203380 A1 | 8/2010 | O'Phelan et al. |
| 2011/0160812 A1 | 6/2011 | Youker et al. |

FOREIGN PATENT DOCUMENTS

| | | |
|---|---|---|
| JP | 2001513679 A | 9/2001 |
| JP | 2002509008 A | 3/2002 |
| JP | 2002239762 A | 8/2002 |
| JP | 2005523129 A | 8/2005 |
| JP | 2006512745 A | 4/2006 |
| JP | 4855071 | 11/2011 |
| JP | 4855071 B2 | 1/2012 |
| WO | WO-9837926 A | 9/1998 |
| WO | WO-98/54739 A1 | 12/1998 |
| WO | WO-9936126 A1 | 7/1999 |
| WO | WO-99/66985 A1 | 12/1999 |
| WO | WO-00/19470 A1 | 4/2000 |
| WO | WO-02/37515 A2 | 5/2002 |
| WO | WO-02/43090 A2 | 5/2002 |
| WO | WO-03/060937 A1 | 7/2003 |
| WO | WO-03090862 A1 | 11/2003 |
| WO | WO-2004062009 A3 | 7/2004 |
| WO | WO-2005070498 A1 | 8/2005 |
| WO | WO-2006/002148 A1 | 1/2006 |
| WO | WO-2008027639 A2 | 3/2008 |
| WO | WO-2008027639 A3 | 3/2008 |

OTHER PUBLICATIONS

"U.S. Appl. No. 11/467,808, Final Office Action mailed Jun. 27, 2011", 12 pgs.

"U.S. Appl. No. 11/467,808, Response filed Apr. 11, 2011 to Non Final Office Action mailed Dec. 9, 2010", 13 pgs.

"U.S. Appl. No. 11/467,808, Response filed Nov. 12, 2010 to Final Office Action mailed Jul. 12, 2010", 12 pgs.
"U.S. Appl. No. 12/764,457, Examiner Interview Summary mailed Mar. 29, 2011", 2 pgs.
"U.S. Appl. No. 12/764,457, Final Office Action mailed Mar. 29, 2011", 11 pgs.
"U.S. Appl. No. 12/764,457, Response filed May 31, 2011 to Final Office Action mailed Mar. 29, 2011", 8 pgs.
"European Application Serial No. 03800396.8, Communication mailed Sep. 1, 2008", 4 pgs.
"European Application Serial No. 03800396.8, Office Action dated Aug. 4, 2011", 4 pgs.
"European Application Serial No. 03800396.8, Office Action mailed Mar. 31, 2010", 4 pgs.
"European Application Serial No. 03800396.8, Office Action Response Filed Aug. 10, 2010", 13 pgs.
"European Application Serial No. 03800396.8, Response filed Dec. 30, 2003 to Communication mailed Sep. 1, 2008", 16 pgs.
"European Application Serial No. 10181460.6, Search Report mailed Mar. 14, 2011", 6 pgs.
"European Application Serial No. 10181466.3, Search Report mailed Mar. 11, 2011", 6 pgs.
"European Application Serial No. 10181475.4, Search Report mailed Mar. 15, 2011", 5 pgs.
"European Application Serial No. 10181482.0, Search Report mailed Mar. 15, 2011", 6 pgs.
"European Application Serial No. 10181514.0, Extended European Search Report mailed Mar. 4, 2011", 5 pgs.
"European Application Serial No. 10181514.0, Response filed Oct. 6, 2011 to EP Search Report dated Mar. 4, 2011", 15 pgs.
"European Application Serial No. 07798278.3, EPO Notice Regarding Amended Claims mailed Apr. 6, 2009", 2 pgs.
"International Application Serial No. PCT/US2003/041704, International Search Report mailed Aug. 29, 2005", 16 pgs.
"International Application Serial No. PCT/US2003/041704, Invitation to Pay Fees and Partial International Search Report mailed Jun. 10, 2005", 15 pgs.
"Japanese Application Serial No. 2005-508647, Notice of Allowance mailed Oct. 4, 2011", (w/ English Translation, 2 pgs.
"Japanese Application Serial No. 2005-508647, Office Action mailed Sep. 21, 2010", (w/ English Translation), 8 pgs.
"Japanese Application Serial No. 2005-508647, Response filed Dec. 20, 2010 to Office Action mailed Sep. 21, 2010", (w/ English Translation of Claims), 39 pgs.
"U.S. Appl. No. 09/165,779, Non-Final Office Action Jan. 18, 2001", 6 pgs.
"U.S. Appl. No. 09/165,779, Non-Final Office Action mailed Apr. 5, 2000", 7 pgs.
"U.S. Appl. No. 09/165,779, Non-Final Office Action mailed Jul. 30, 2002", 6 pgs.
"U.S. Appl. No. 09/165,779, Notice of Allowance mailed Jul. 5, 2001", 5 pgs.
"U.S. Appl. No. 09/165,779, Notice of Allowance mailed Sep. 6, 2000", 5 pgs.
"U.S. Appl. No. 09/165,779, Notice of Allowance mailed Nov. 7, 2002", 7 pgs.
"U.S. Appl. No. 09/165,779, Response filed Feb. 22, 2000 to Restriction Requirement mailed Jan. 19, 2000", 5 pgs.
"U.S. Appl. No. 09/165,779, Response filed Apr. 18, 2001 to Non-Final Office Action mailed Jan. 18, 2001", 17 pgs.
"U.S. Appl. No. 09/165,779, Response filed Aug. 4, 2000 to Non-Final Office Action mailed Apr. 5, 2000", 7 pgs.
"U.S. Appl. No. 09/165,779, Response filed Aug. 30, 2002 to Non-final Office Action mailed Jul. 30, 2002", 14 pgs.
"U.S. Appl. No. 09/165,779, Restriction Requirement mailed Jan. 19, 2000", 4 pgs.
"U.S. Appl. No. 10/360,551, Advisory Action mailed Jul. 7, 2006", 3 pgs.
"U.S. Appl. No. 10/360,551, Appeal Brief filed Feb. 14, 2007", 20 pgs.
"U.S. Appl. No. 10/360,551, Decision on Appeal mailed Aug. 28, 2008", 7 pgs.
"U.S. Appl. No. 10/360,551, Examiner's Answer mailed May 10, 2007", 10 pgs.
"U.S. Appl. No. 10/360,551, Final Office Action mailed Apr. 14, 2006", 8 pgs.
"U.S. Appl. No. 10/360,551, Non-Final Office Action mailed Jan. 6, 2006", 6 pgs.
"U.S. Appl. No. 10/360,551, Notice of Allowance mailed Sep. 11, 2008", 6 pgs.
"U.S. Appl. No. 10/360,551, Pre-Appeal Brief Request filed Sep. 14, 2006", 5 pgs.
"U.S. Appl. No. 10/360,551, Reply Brief filed Jul. 10, 2007", 4 pgs.
"U.S. Appl. No. 10/360,551, Response filed Apr. 6, 2006 to Non-Final Office Action mailed Jan. 6, 2006", 7 pgs.
"U.S. Appl. No. 10/360,551, Response filed Jun. 14, 2006 to Final Office Action mailed Apr. 14, 2006", 8 pgs.
"U.S. Appl. No. 10/360,551, Response filed Nov. 14, 2005 to Restriction Requirement mailed Oct. 14, 2005", 5 pgs.
"U.S. Appl. No. 10/360,551, Restriction Requirement mailed Oct. 14, 2005", 12 pgs.
"U.S. Appl. No. 11/117,952, Final Office Action mailed Apr. 24, 2008", 10 pgs.
"U.S. Appl. No. 11/117,952, Non-Final Office Action Mailed Sep. 25, 2007", 9 pgs.
"U.S. Appl. No. 11/117,952, Response filed Aug. 24, 2007 to Restriction Requirement mailed Jul. 24, 2007", 7 pgs.
"U.S. Appl. No. 11/117,952, Response filed Dec. 26, 2007 to Non-Final Office Action mailed Sep. 25, 2007", 9 pgs.
"U.S. Appl. No. 11/117,952, Restriction Requirement mailed Jul. 24, 2007", 6 pgs.
"U.S. Appl. No. 11/467,808, Final Office Action mailed Jul. 12, 2010", 10 pgs.
"U.S. Appl. No. 11/467,808, Non-Final Office Action mailed Apr. 8, 2009", 10 pgs.
"U.S. Appl. No. 11/467,808, Non-Final Office Action mailed Dec. 9, 2009", 8 pgs.
"U.S. Appl. No. 11/467,808, Non-Final Office Action mailed Dec. 9, 2010", 10 pgs.
"U.S. Appl. No. 11/467,808, Response filed Mar. 5, 2009 to Restriction Requirement mailed Feb. 5, 2009", 9 pgs.
"U.S. Appl. No. 11/467,808, Response filed Aug. 6, 2009 to Non-Final Office Action mailed Apr. 8, 2009", 14 pgs.
"U.S. Appl. No. 11/467,808, Restriction Requirement mailed Feb. 5, 2009", 7 pgs.
"U.S. Appl. No. 12/178,876, Non-Final Office Action mailed Dec. 31, 2009", 9 pgs.
"U.S. Appl. No. 12/178,876, Notice of Allowance mailed Jul. 27, 2010", 6 pgs.
"U.S. Appl. No. 12/178,876, Notice of Allowance mailed Nov. 17, 2010", 6 pgs.
"U.S. Appl. No. 12/178,876, Response filed Apr. 30, 2010 to Non-Final Office Action mailed Dec. 31, 2009", 9 Pgs.
"U.S. Appl. No. 12/178,876, Response filed Aug. 14, 2009 to Restriction Requirement mailed Jul. 14, 2009", 7 pgs.
"U.S. Appl. No. 12/178,876, Restriction Requirement mailed Jul. 14, 2009", 6 pgs.
"U.S. Appl. No. 12/355,242, Final Office Action mailed Oct. 22, 2009", 10 pgs.
"U.S. Appl. No. 12/355,242, Non-Final Office Action mailed Apr. 30, 2009", 8 pgs.
"U.S. Appl. No. 12/355,242, Response filed Jul. 29, 2009 to Non-Final Office Action mailed Apr. 30, 2009", 11 pgs.
"U.S. Appl. No. 12/355,242, Response filed Dec. 10, 2009 to Final Office Action mailed Oct. 22, 2009", 8 pgs.
"U.S. Appl. No. 12/764,457, Non-Final Office Action mailed Oct. 29, 2010", 11 pgs.
"U.S. Appl. No. 12/764,457, Response filed Jan. 31, 2011 to Non-Final Office Action mailed Oct. 29, 2010", 9 pgs.
"U.S. Appl. No. 12/764,457, Response filed Sep. 16, 2010 to Restriction Requirement mailed Jul. 16, 2010", 6 pgs.
"U.S. Appl. No. 12/764,457, Restriction Requirement mailed Jul. 16, 2010", 7 pgs.
"U.S. Appl. No. 13/041,651, Notice of Allowance mailed Sep. 6, 2011", 5 pgs.

"International Application No. PCT/US2003/041704, Invitation to Pay Additional fees and Partial International Search mailed Jun. 10, 2005", 16 pgs.

"International Application No. PCT/US2007/070697, International Search Report mailed Mar. 4, 2008", 4 pgs.

"International Application No. PCT/US2007/070697, Written Opinion mailed Mar. 4, 2008", 8 pgs.

Fishbane, et al., "Physics for Scientists and Engineers,", Prentice-Hall, Inc., vol. II,, (1993,), 791-793.

Haasl, Benjamin J, et al., "Insulative Member on Battery Cathode", U.S. Appl. No. 11/140,854, filed May 31, 2005, 30 pgs.

Kelley, Shawn, et al., "Method and Apparatus for Porous Insulative Film for Insulating Energy Source Layers", U.S. Appl. No. 11/127,025, filed May 11, 2005, 21 pgs.

Lunsman, P., et al., "High Energy Density Capacitors for Implantable Defibrillators", Proceedings of the 16th Capacitor and Resistor Technology Symposium, Monteleone Hotel, New Orleans, Louisiana, (Mar. 11-15, 1996), pp. 277-280.

O'Phelan, Michael J, "Batteries Including a Flat Plate Design", U.S. Appl. No. 60/437,537, filed Dec. 31, 2002, 116 pgs.

Schmidt, Brian L, et al., "Configurations and Methods for Making Capacitor Connections", U.S. Appl. No. 09/706,576, filed Nov. 3, 2000, 26 pgs.

Sherwood, Gregory J., "Method and Apparatus for High Voltage Aluminum Capacitor Design", U.S. Appl. No. 60/588,905, filed Jul. 16, 2004, 241 pgs.

Youker, Nick A, "Method and Apparatus for an Implantable Pulse Generator With a Stacked Battery and Capacitor", U.S. Appl. No. 11/117,952, filed Apr. 29, 2005, 21 pgs.

"U.S. Appl. No. 11/467,808, Examiner Interview Summary mailed Mar. 28, 2011", 4 pgs.

"U.S. Appl. No. 11/467,808, Response filed Apr. 8, 2010 to Non Final Office Action mailed Dec. 9, 2009", 10 pgs.

"U.S. Appl. No. 12/178,876, Preliminary Amendment mailed Jan. 21, 2009", 7 pgs.

"European Application Serial No. 03800396.8, Office Action Response filed Dec. 12, 2011", 2 pgs.

"European Application Serial No. 10181415.0, Office Action mailed Apr. 27, 2012", 4 pgs.

"European Application Serial No. 10181415.0, Office Action Response filed Oct. 13, 2011", 9 pgs.

"European Application Serial No. 10181460.6, Extended Search Report Response filed Nov. 18, 2011", 13 pgs.

"European Application Serial No. 10181460.6, Office Action mailed Apr. 30, 2012", 4 pgs.

"European Application Serial No. 10181466.3, Office Action mailed Apr. 24, 2012", 6 pgs.

"European Application Serial No. 10181466.3, Response filed Nov. 8, 2011 to European Search Report mailed Mar. 11, 2011", 13 pgs.

"European Application Serial No. 10181475.4, Extended Search Report Response filed Nov. 17, 2011", 14 pgs.

"European Application Serial No. 10181475.4, Office Action mailed May 9, 2012", 4 pgs.

"European Application Serial No. 10181482.0, Office Action mailed Apr. 26, 2012", 4 pgs.

"European Application Serial No. 10181482.0, Response filed Nov. 18, 2011 to Office Action mailed May 23, 2011", 12 pgs.

"European Application Serial No. 10181493.7, Office Action mailed Jan. 20, 2012", 6 pgs.

"European Application Serial No. 10181504.1, Office Action mailed Apr. 16, 2012", 4 pgs.

"European Application Serial No. 10181504.1, Response filed Oct. 13, 2011 to Office Action mailed Mar. 9, 2011", 14 pgs.

"European Application Serial No. 10181514.0, Examination Notification Art. 94(3) mailed Mar. 30, 2012", 4 pgs.

"Japanese Application Serial No. 2009-526779, Office Action mailed Apr. 13, 2012", (w/ English Translation), 13 pgs.

"Japanese Application Serial No. 2009-526779, Response filed Jul. 13, 2012 to Office Action mailed Apr. 13, 2012", (w/ English Translation of Amended Claims), 10 pgs.

IMPLANTABLE PULSE GENERATOR WITH A STACKED BATTERY AND CAPACITOR

CROSS REFERENCE TO RELATED APPLICATIONS

This application is a continuation of U.S. application Ser. No. 13/041,651, filed Mar. 7, 2011, now issued as U.S. Pat. No. 8,055,346, which is a divisional of U.S. application Ser. No. 12/178,876, filed Jul. 24, 2008, now issued as U.S. Pat. No. 7,917,207, which is a continuation of U.S. application Ser. No. 11/117,952, filed Apr. 29, 2005, now abandoned, the specifications of which are herein incorporated by reference.

The following commonly assigned U.S. Patents are related to the present application and are incorporated herein by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov 3, 2000, issued Mar. 2, 2004. Additionally, the present application is related to the following commonly assigned U.S. Patent Publication which is incorporated herein by reference in its entirety: "Method and Apparatus for Single High Voltage Aluminum Capacitor Design," Ser. No. 60/588,905, filed on Jul. 16, 2004. Further, the present application is related to the following commonly assigned U.S. Patent Application which is incorporated by reference in its entirety: "Batteries Including a Flat Plate Design," U.S. patent application Ser. No. 10/360,551 filed Feb. 7, 2003, now issued as U.S. Pat. No. 7,479,349, which claims the benefit under 35 U.S.C 119(e) of U.S. Provisional Application Ser. No. 60/437,537 filed Dec. 31, 2002.

TECHNICAL FIELD

This disclosure relates generally to batteries and capacitors, and more particularly, to method and apparatus for an implantable pulse generator with a stacked battery and capacitor.

BACKGROUND

There is an ever-increasing interest in making electronic devices physically smaller. Consequently, electrical components become more compact as technologies are improved. However, such advances in technology also bring about additional problems. One such problem involves efficient packaging of components.

Components such as batteries, capacitors, and various additional electronics are often packaged together in electrical devices. As such, there is a need in the art for improved packaging strategies. Improvement could be realized by an overall increase in the efficiency of component packaging in existing devices. But improved systems must be robust and adaptable to various manufacturing processes.

SUMMARY

The above-mentioned problems and others not expressly discussed herein are addressed by the present subject matter and will be understood by reading and studying this specification.

One embodiment of the present subject matter includes a method of stacking flat battery layers into a battery stack; positioning the battery stack in a battery case, the planar battery surface having a battery perimeter; stacking flat capacitor layers into a capacitor stack; positioning the capacitor stack in a capacitor case, the planar capacitor surface having a capacitor perimeter; disposing the flat battery case and the flat electrolytic capacitor case in stacked alignment in a housing for implantation such that the battery perimeter and the capacitor perimeter are substantially coextensive; and hermetically sealing the housing.

Additionally, one embodiment of the present subject matter includes a battery having a plurality of flat battery layers disposed in a battery case, the battery case having a planar battery surface which has a battery perimeter; and a capacitor including a plurality of flat capacitor layers disposed in a capacitor case, the capacitor case having a planar capacitor surface which has a capacitor perimeter, the capacitor stacked with the battery such that the planar battery surface and the planar capacitor surface are adjacent, with the capacitor perimeter and the battery perimeter substantially coextensive; and a hermetically sealed implantable housing having a first shell and a lid mated to the first shell at a first opening, the first opening sized for passage of the battery and the capacitor, wherein the battery and the capacitor are disposed in the hermetically sealed implantable housing.

One embodiment of the present subject matter includes an apparatus having a hermetically sealed implantable device housing having a lid mated to an opening; programmable pulse generation electronics disposed in the hermetically sealed implantable device housing, the programmable pulse generation electronics sized for passage through the opening; battery means for powering the programmable pulse generation electronics, the battery means sized for passage through the opening; and capacitor means electrically interconnected to the battery means, the capacitor means for powering the programmable pulse generation electronics and sized for passage through the opening.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Implantable medical devices are now in wide use for treating a variety of diseases. Cardiac rhythm management devices, as well as other types of implantable medical devices, are powered by a battery and a capacitor contained within the housing of the device. The size and shape of a battery which supplies sufficient power to operate the device is one factor which affects how small and physiologically shaped the housing of the device can be made. This is true for the capacitor as well. The present disclosure relates to a battery and capacitor and method for their construction, each suitable for use in an electronic device. Various embodiments are adapted for use in an implantable medical device. Overall, the present subject matter affords designers more freedom in packaging electronic device components into a housing.

Figure 1A:
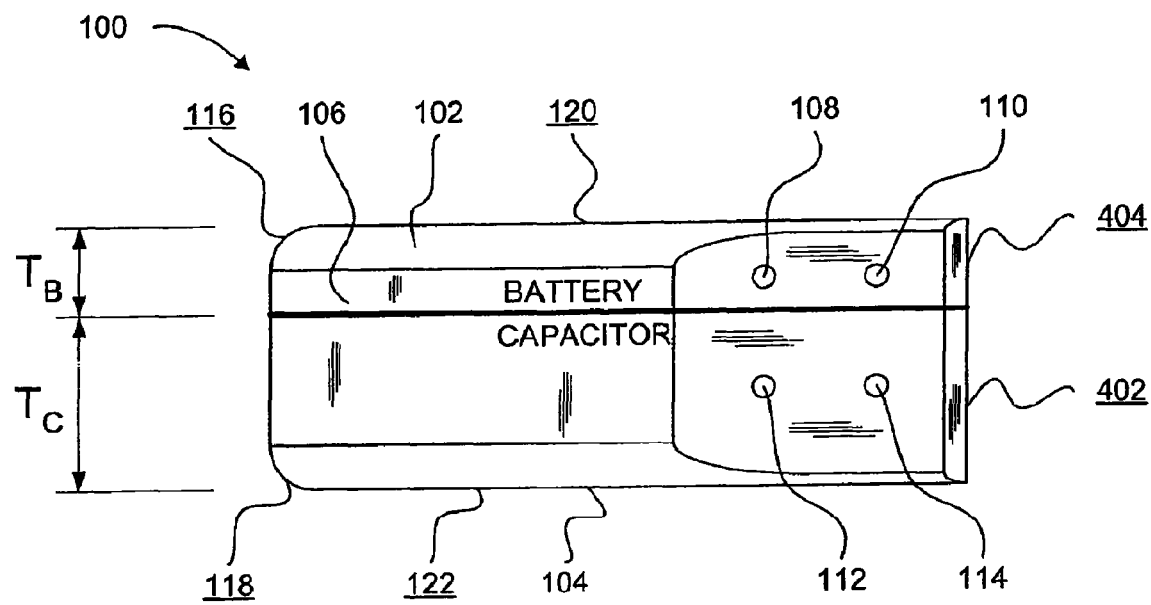
FIG. 1A is a side view of a power source, according to one embodiment of the present subject matter.

FIG. 1A is a side view of a power source 100, according to one embodiment of the present subject matter. In various embodiments, an example battery 102 includes a contour 116, which allows for positioning the battery 102 in various devices. For example, in various embodiments, battery 102 is shaped for placement in device adapted for chronic implantation. Additionally, in various embodiments, the battery 102 includes a feedthrough port 108, which is adapted for passage of one or more conductors. In various embodiments, the conductors at the feedthrough port 108 are connected to the battery anode. The battery additionally includes a feedthrough port 110 which, in various embodiments, is connected to the battery cathode. In some embodiments, a single feedthrough port is used instead of two feedthrough ports. Other embodiments include one or more feedthrough ports and a backfill port.

In various embodiments, the example capacitor 104 includes a contour 118, which allows for positioning the capacitor 104 in various devices. For example, in various embodiments, capacitor 104 is shaped for placement in a device adapted for chronic implantation. Additionally, in various embodiments, the capacitor 104 includes a feedthrough port 112, which is adapted for passage of one or more conductors. In various embodiments, the conductors at the feedthrough port 112 comprise a portion of the anode of the capacitor. The capacitor additionally includes a feedthrough port 114 which, in various embodiments, is connected to the battery cathode. In some embodiments, a single feedthrough port is used instead of two feedthrough ports. Other embodiments include one or more feedthrough ports and a backfill port.

In various embodiments, a device housing into which a battery and capacitor may be disposed has an interior. In some of these embodiments, the device interior has a first major interior face and a second major interior face. Battery and capacitor combinations can be shaped to mate to these faces. For example, in one embodiment, a battery face 120 is adapted for abutting an interior face of a housing. In some embodiments, the housing and the battery face 120 are separated from a housing by an insulator. The capacitor includes a face 122 which also is adapted for abutting an interior surface of a housing. Sidewall 402 and sidewall 404 are adapted for placement adjacent additional device components, in various embodiments.

Various embodiments maintain a continuous surface from sidewall 402 to sidewall 404. In various embodiments, the seam 106 defined by the adjacent battery 102 and capacitor 104 extends along a continuous surface. Thus, in various embodiments, the combined capacitor and battery are adapted for space efficient placement in a housing. In various embodiments, the housing is only marginally larger than the combined capacitor and battery so that the housing may accommodate those components. As such, various embodiments enable packaging additional devices in the housing adjacent the battery capacitor combination.

Battery 102 has a thickness $T_B$, in various embodiments. In various embodiments, the thickness is measured orthogonally, extending between interface 106 and surface 120. Additionally, capacitor 104 has a thickness $T_C$, in various embodiments. The thickness is measured orthogonally, extending between interface 106 and surface 122, in various embodiments. In various embodiments, the thicknesses $T_B$ and $T_C$ are selectable to fill the volume of a device housing. For example, in one embodiment, the present subject matter creates an index of a plurality of flat capacitors, the index created by measuring the thickness $T_C$ of each flat capacitor and storing that thickness in a first index. Additionally, in various embodiments, the present subject matter creates an index of a plurality of flat batteries, the index created by measuring the thickness $T_B$ of each flat battery and storing that thickness in a second index. The present subject matter than selects a battery and a capacitor having respective thicknesses $T_B$, $T_C$ selected to fill the volume of the targeted device housing.

Figure 1B:
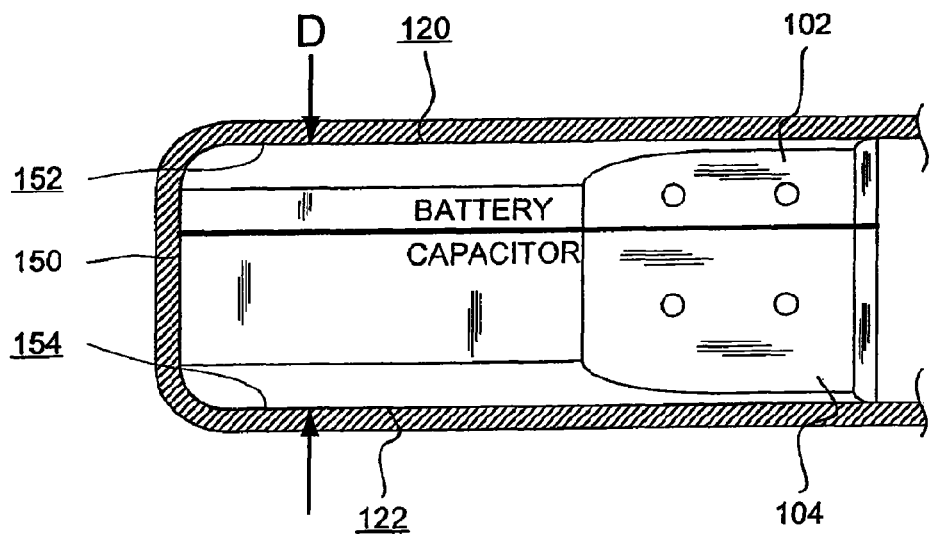
FIG. 1B illustrates a partial cross section of a device housing, a battery, and a capacitor, according to one embodiment of the present subject matter.

FIG. 1B illustrates a partial cross section of a device housing 150, a battery 102, and a capacitor 104, according to one embodiment of the present subject matter. In various embodiments, distance D extends between a first interior surface 152 for abutting a battery face 120, and a second interior surface 154 adapted for abutting surface 122. In various embodiments, the present subject matter selects a capacitor from a first index, and a battery from a second index, such that the combined thickness of the battery and the capacitor substantially match the thickness D. Additionally, in various embodiments, the selection of battery thickness and capacitor thickness is made in light of the thickness of adhesive layer and/or insulative layers disposed between the battery and the capacitor, and between these respective subcomponents and the device housing. In varying embodiments, the ratio between capacitor thickness and battery thickness is from about 7:1 to about 1.5:1. In additional embodiment, the ratio between the capacitor thickness and the battery thickness is from about 6:1 to about 2:1. Other ratios are possible without departing from the scope of the present subject matter.

In various embodiments, indexing of battery thickness, capacitor thickness, battery perimeter, capacitor perimeter, and other power source parameters is performed using a programmable computer. The present subject matter is not limited to indexes managed by programmable computers, however, as other indexing systems are within the scope of the present subject matter.

Figure 2:
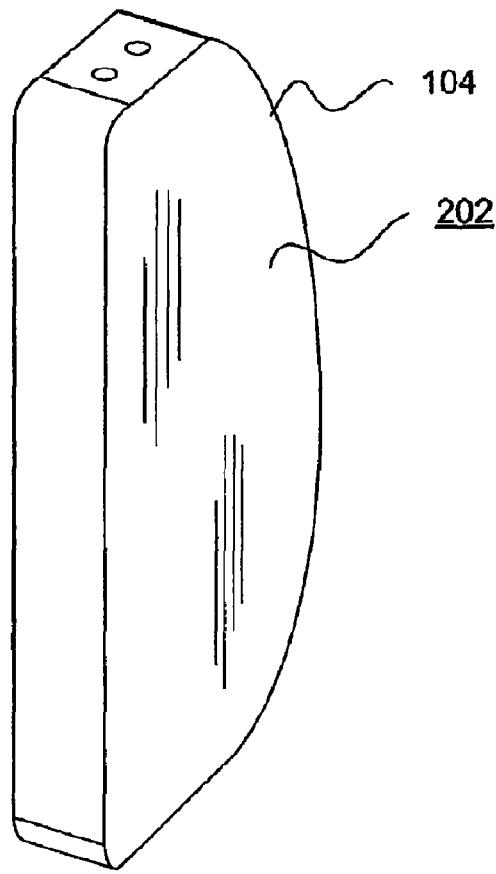
FIG. 2 is a perspective view of a capacitor, according to one embodiment of the present subject matter.

FIG. 2 is a perspective view of a capacitor, according to one embodiment of the present subject matter. Substantially flat electrolytic capacitors, in various examples, include a plurality of capacitor layers stacked together. In various embodiments, these stacks of capacitors are assembled into a capacitor case. Various cases are conductive or nonconductive. Some cases include feedthroughs through which conductors pass. The present subject matter includes, but is not limited to, embodiments, one of which is shown in FIG. 6, disclosed on or around pages 12-37, 39, 41-140 of the following related and commonly assigned Provisional U.S. Patent Application "Method and Apparatus for Single High Voltage Aluminum Capacitor Design," Ser. No. 60/588,905, filed on Jul. 16, 2004, incorporated herein by reference.

In various embodiments, the present subject matter includes a flat electrolytic capacitor 104 with a planar capacitor surface 202. In various embodiments, the planar capacitor surface includes a capacitor perimeter. In various embodiments, the capacitor stack is adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

However, in some embodiments, the stack is disposed in a case, and linked with other components, a state which affects energy density in some embodiments. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules. In various embodiments, these ranges are available at a voltage of between about 410 volts to about 610 volts.

Although these ranges embody one example possible within the scope of the subject matter, the subject matter is not so limited, and other capacitors without departing from the scope of the present subject matter.

Figure 3:
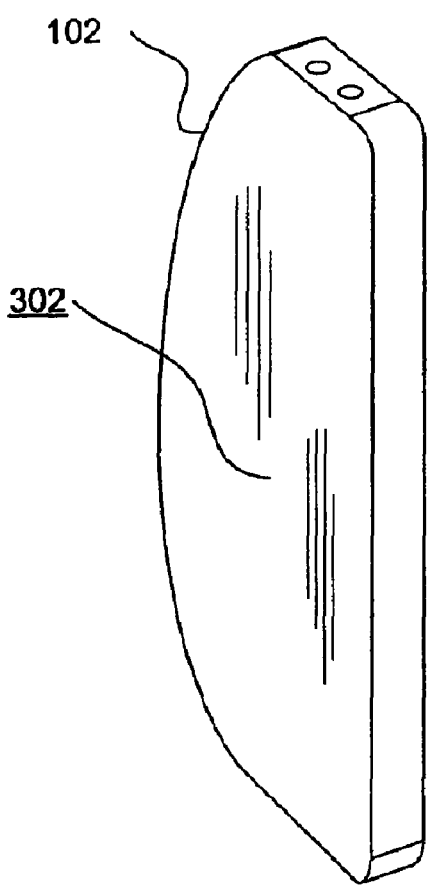
FIG. 3 is a perspective view of a battery, according to one embodiment of the present subject matter.

FIG. 3 is a perspective view of a battery, according to one embodiment of the present subject matter. In various embodiments, the battery 102 of the present subject matter is substantially flat. Substantially flat batteries, in various examples, include a plurality of battery electrodes stacked together, and further assembled into a battery case. Various battery cases are conductive or nonconductive. Some battery cases include feedthroughs. In various embodiments, the battery cases include a planar battery surface 302. The present subject matter includes, but is not limited to, embodiments disclosed at paragraphs 0095-0110, 0136-0196, 0206-0258 of the following related and commonly assigned U.S. patent application, "Batteries Including a Flat Plate Design," U.S. patent application Ser. No. 10/360,551, filed on Feb. 7, 2003, incorporated herein by reference.

Figure 4:
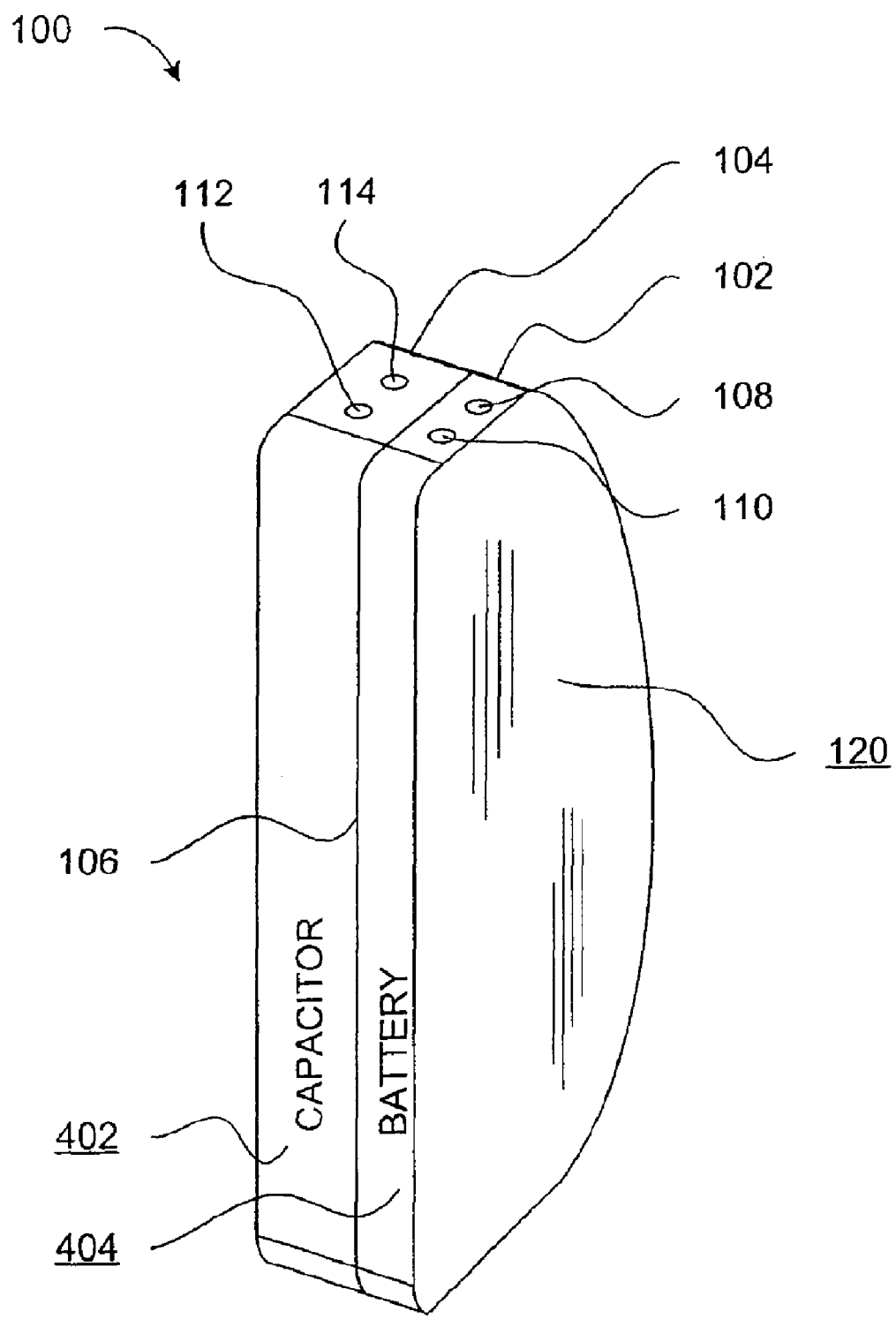
FIG. 4 is a perspective view of a battery and a capacitor, according to one embodiment of the present subject matter.

FIG. 4 is a perspective view of a battery and a capacitor, according to one embodiment of the present subject matter. In various embodiments, the present subject matter includes a power source 100 which has a battery 102 and a capacitor 104 mated at an interface 106, at which a planar battery surface and a planar capacitor surface are substantially coextensive. As a result of alignment, various embodiments demonstrate an overall envelope which is substantially continuous. Additionally, in various embodiments, the battery 102 includes a feedthrough ports 108, 110. Capacitor 104 includes feedthrough ports 112, 114, in various embodiments.

Various capacitor embodiments include a capacitor sidewall 402, and various battery embodiments include a battery sidewall 404. Various embodiments additionally include a battery face 120. A capacitor face is not visible in the illustration due to the orientation of the figure. In various examples, each of these respective case features is planar. When placed adjacent to one another, various embodiments include features which form a substantially planar overall sidewall which is the sum of each of the individual surfaces.

In various embodiments, the overall surface is continuous. For example, sidewalls 402, 404 form a continuous surface. A continuous surface may have a linear shape, or a curvilinear shape. Embodiments having a continuous overall sidewall are within the scope of the present subject matter, however, additional embodiments are possible without departing from the scope of the scope of the present subject matter.

Figure 5:
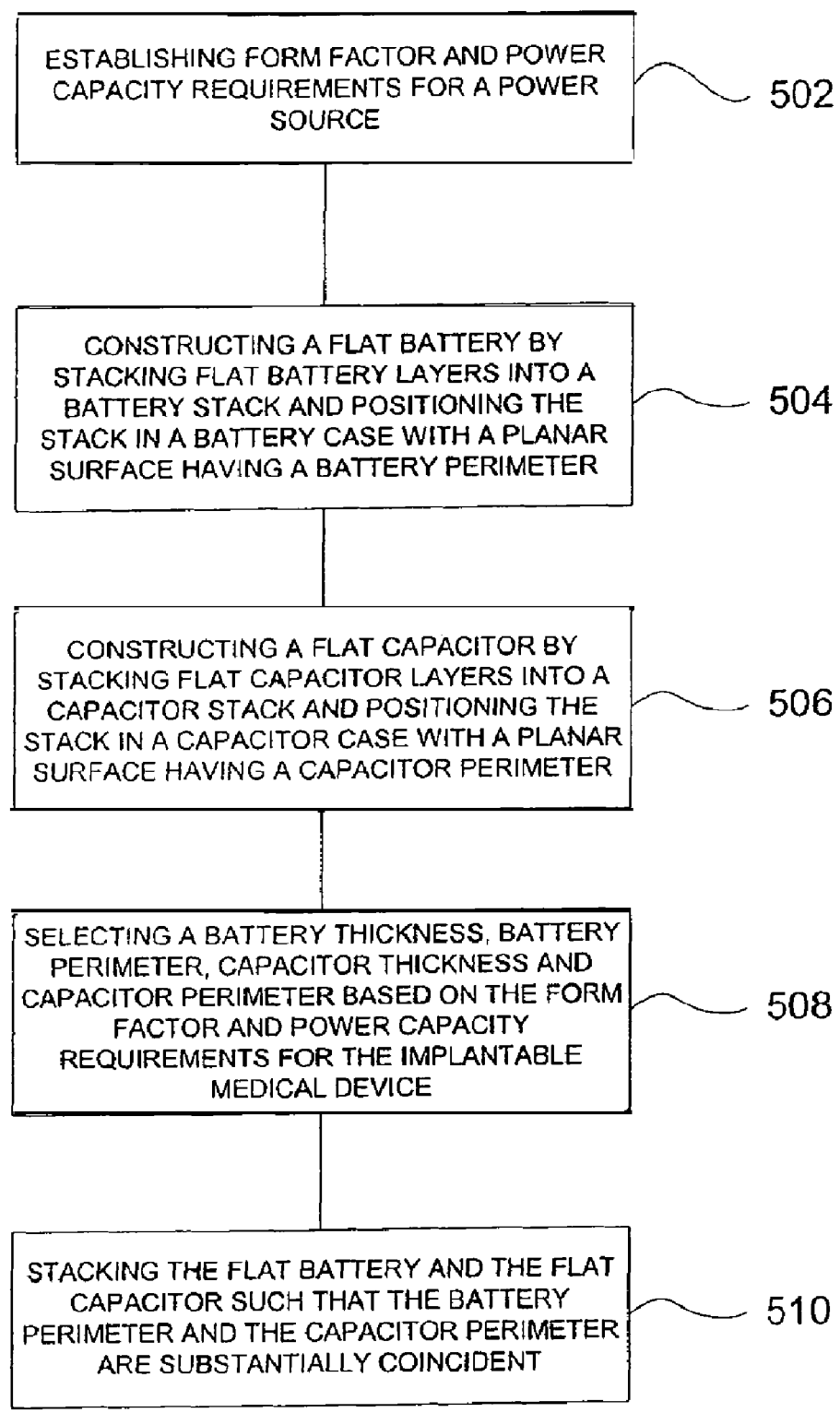
FIG. 5 is a method for constructing a battery and capacitor power source, according to one embodiment of the present subject matter.

FIG. 5 is a method for constructing a battery and capacitor power source, according to one embodiment of the present subject matter. In one embodiment of the present subject matter, the process includes establishing form factor and power capacity requirements for a power source to be used in an implantable medical device 502. The embodiment includes constructing a flat battery by stacking flat battery layers into a battery stack and positioning the stack in a battery case with a planar interface and a battery perimeter and battery thickness 504. The embodiment further includes constructing a flat electrolytic capacitor by stacking flat capacitor layers into a capacitor stack and positioning the stack in a capacitor case with a planar interface and a capacitor perimeter and capacitor thickness 506. The embodiment additionally includes stacking the flat battery and the flat electrolytic capacitor such that the battery perimeter and the capacitor perimeter are substantially coextensive 510. This embodiment is illustrative of the present subject matter, but it should be noted that other combinations of steps, and additional steps, also lie within the scope of the present subject matter.

For example, in some embodiments, a battery thickness, battery perimeter, capacitor thickness and capacitor perimeter are selected based on form factor and power capacity requirements for an implantable medical device 508. Additionally, various method embodiments include measuring a ratio between battery thickness and capacitor thickness, and using this ratio in selecting a battery and capacitor. A ratio is be established by known power requirements, in various embodiments. Another example combines size requirements with power requirements in selecting a ratio. The ratio can be stored and used by a design process or manufacturing process to discern the mechanical and electrical composition of a needed power source, in various embodiments.

In various embodiments, the present subject matter includes delivering from the flat battery and the flat electrolytic capacitor from about 1.25 Joules per Amp hour of battery capacity to about 50 Joules per amp hour of battery capacity. In some of these embodiments, the flat battery has a battery capacity density of from about 0.23 amp hours per cubic centimeter of flat battery to about 0.25 amp hours per cubic centimeter of flat battery. Battery capacity density is measured by dividing the amp-hour rating of the battery by the battery volume, in various embodiments. The present subject matter includes, but is not limited to, embodiments disclosed at paragraphs 0095-0110, 0136-0196, 0206-0258 of the following related and commonly assigned U.S. Patent Publication, "Batteries Including a Flat Plate Design," U.S. Patent Publication No. 2004/0127952, filed on Feb. 7, 2003, incorporated herein by reference.

In additional embodiments, the flat electrolytic capacitor includes an energy density of from about 4.65 joules per cubic centimeter of flat electrolytic capacitor to 6.5 joules per cubic centimeter of flat electrolytic capacitor. The present subject matter includes, but is not limited to, embodiments disclosed on or around pages 12-37, 39, 41-140 of the following related and commonly assigned Provisional U.S. Patent Application "Method and Apparatus for Single High Voltage Aluminum Capacitor Design," Ser. No. 60/588,905, filed on Jul. 16, 2004, incorporated herein by reference.

Various methods of the present subject matter benefit from selecting capacitor stack layers and battery stack layers which are substantially parallel to their coextensive case interfaces. By constructing the power source as such, various benefits are possible. For example, in one embodiment, a single two-axis machine can position capacitor layers in a stack, position the capacitor stack in a capacitor case, position battery layers in a stack, and position the battery stack in a battery case. In one embodiment, the single two-axis machine is a pick-and-place machine. This combination is provided for illustration, but other combinations of these steps are possible, and additional steps are also within the scope of the present subject matter.

FIG. 6 shows a section view of capacitor 3100 taken along line 2-2, shows that modules 3102a-3102e are staggered in two dimensions. In this view, capacitor modules 3102a-3102e define a profile 3108, which is generally congruent to a curved portion 3104b of case 3104. Although profiles 3106 and 3108 are quite distinct in this exemplary embodiment, other embodiments make profiles 3106 and 3108 substantially congruent.

In one embodiment, each capacitor module includes a three-layer etched and/or perforated anode, a cathode, and at least one electrolyte-carrying separator between the anode and the cathode. The anode and cathode comprise foils of aluminum, tantalum, hafnium, niobium, titanium, zirconium, or combinations of these metals. Additionally, each capacitor module is sandwiched between two pairs of electrolyte-carrying separators, with the separators extending beyond the anode and cathode to prevent undesirable shorting with the case. Alternatively, separate insulative layer can be placed between the capacitor modules and the case interior walls to prevent shorting.

In other embodiments, the capacitor modules take other forms having different numbers of anode layers and separators. For example, in some embodiments, the anodes, cathode, and separators in one or more of the capacitor modules are staggered to define curved module faces that confront the interior surfaces 3104a or 3104b of the case. Also, in some embodiments, one or more of the anodes or cathodes are coupled to the case, making it either anodic or cathodic.

To define the staggered edge faces and thus the curved profile, some embodiments which provide the curved profile in a single dimension, use a set of generally congruent modules of different sizes. For example, one embodiment includes four generally D-shaped modules, each with a common width and height, but with four successively smaller lengths. The modules are stacked, each module having at least one edge aligned vertically with the corresponding edges of adjacent modules.

FIG. 7 shows front view of stack 24 of FIG. 21. Here it can be seen that in one embodiment, the present system allows for the use of non-uniform layers of a battery. In this example, generally designated are a top stack portion 24A, a middle stack portion 24B and a bottom stack portion 24C. Each of the stack portions 24A-24C includes one or more cathode layers, separator layers, and anode layers. The layers of top portion 24A have at least one dimension which is smaller than the similar layers in middle stack portion 24B. Likewise, bottom stack portion 24C includes at least one dimension smaller than similar layers in middle stack portion 24B. This dimensional difference results in the curved profile of stack 24.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

What is claimed is:

1. An apparatus, comprising:
a battery including a plurality of flat battery electrode layers disposed in a battery case, the battery case having a planar battery surface which has a battery interface perimeter;
a capacitor including a plurality of flat capacitor electrode layers disposed in a capacitor case that is separate from the battery case, the capacitor case having a planar capacitor surface which has a capacitor interface perimeter; and
a hermetically sealed implantable housing having a first shell and a lid mated to the first shell at a first opening, the first opening sized for passage of the battery and the capacitor, the implantable housing defining a housing interior,
wherein the battery and the capacitor are disposed in the hermetically sealed implantable housing, and the capacitor is stacked with the battery such that the planar battery surface and the planar capacitor surface are adjacent, with the capacitor interface perimeter and the battery interface perimeter substantially coextensive, and wherein the battery and the capacitor define a power source form factor with an exterior contour including an exterior battery contour and an exterior capacitor contour, the exterior contour being continuous and substantially matching at least a portion of the housing interior,
wherein at least one of the plurality of flat battery electrode layers has an outer battery perimeter that is smaller than the battery interface perimeter, with the exterior of the battery case contoured to curve from the outer battery perimeter toward the battery interface perimeter, and
wherein at least one of the plurality of flat capacitor electrode layers has a outer capacitor perimeter that is smaller than the capacitor interface perimeter, with the exterior of the capacitor case contoured to curve from the outer capacitor perimeter toward the capacitor interface perimeter.

2. The apparatus of claim 1, wherein the battery and the capacitor and are adapted to deliver from about 1.25 joules per amp hour of battery capacity to about 50 joules per amp hour of battery capacity.

3. The apparatus of claim 2, wherein the flat battery includes a battery capacity density of from about 0.23 amp hours per cubic centimeter to about 0.25 amp hours per cubic centimeter.

4. The apparatus of claim 2, wherein the capacitor includes an energy density of from about 4.65 joules per cubic centimeter to 6.5 joules per cubic centimeter.

5. The apparatus of claim 1, further comprising:
a battery face of the battery extending parallel the planar battery surface, with a battery sidewall extending between the battery face and the planar battery surface; and
a capacitor face of the capacitor, with a capacitor sidewall extending between the capacitor face and the capacitor face,
wherein the battery sidewall and the capacitor sidewall define a continuous surface.

6. The apparatus of claim 1, wherein the plurality of flat battery layers are disposed parallel the planar battery surface of the battery case.

7. The apparatus of claim 6, wherein the plurality of flat capacitor layers are disposed parallel the planar capacitor surface of the capacitor case.

8. An apparatus, comprising:
a battery including a plurality of flat battery layers disposed in a battery case, the battery case having a battery case wall defining a planar battery surface which has a battery perimeter and which is substantially parallel to the plurality of flat battery layers, with a battery face of the battery opposing the planar battery surface, with a battery sidewall extending between the battery face and the planar battery surface;
a capacitor including a plurality of flat capacitor layers disposed in a capacitor case, the capacitor case having a capacitor case wall defining a planar capacitor surface which has a capacitor perimeter and which is substantially parallel to the plurality of flat capacitor layers, with a capacitor face opposing the planar capacitor surface, with a capacitor sidewall extending between the capacitor face and the planar capacitor surface; and
a hermetically sealed implantable housing having a first shell and a lid mated to the first shell at a first opening, the first opening sized for passage of the battery and the capacitor, the implantable housing defining a housing interior;
wherein the battery case and the capacitor case are separate and stacked onto one another with the planar battery surface and the planar capacitor surface confronting one another and coextensive with one another, with the battery sidewall and the capacitor sidewall defining a continuous surface substantially matching at least a portion of the housing interior and with the battery case wall and the capacitor case wall each disposed between the plurality of flat battery layers and the plurality of flat capacitor layers.

9. The apparatus of claim 8, wherein the capacitor has a thickness measured from the capacitor face to the planar capacitor surface, and the battery has a thickness measured from the battery face to the planar battery surface, and the ratio between capacitor thickness and battery thickness is from about 7:1 to about 1.5:1.

10. The apparatus of claim 8, wherein the capacitor is an electrolytic capacitor.

11. The apparatus of claim 8, wherein the battery sidewall and the capacitor sidewall define a continuous surface which is substantially planar.

12. The apparatus of claim 8, wherein the plurality of flat battery layers are disposed parallel the planar battery surface of the battery case.

13. The apparatus of claim 12, wherein the plurality of flat capacitor layers are disposed parallel the planar capacitor surface of the capacitor case.

14. The apparatus of claim 8, wherein the battery and the capacitor and are adapted to deliver from about 1.25 joules per amp hour of charge to about 50 joules per amp hour of charge.

15. The apparatus of claim 14, wherein the flat battery includes a battery capacity density of from about 0.23 amp hours per cubic centimeter to about 0.25 amp hours per cubic centimeter.

16. The apparatus of claim 14, wherein the capacitor includes an energy density of from about 4.65 joules per cubic centimeter to 6.5 joules per cubic centimeter.

17. An apparatus, comprising:
a battery including a plurality of flat battery layers disposed in a battery case, the battery case having a battery case wall defining a planar battery surface;
an electrolytic capacitor including a plurality of flat capacitor layers disposed in a capacitor case separate from the battery case, the capacitor case having a capacitor case wall defining a planar capacitor surface, the capacitor case stacked with the battery case such that the planar battery surface and the planar capacitor surface are facing each other and abutting, with the battery case wall and the capacitor case wall each disposed between the plurality of flat battery layers and the plurality of flat capacitor layers; and
a hermetically sealed implantable housing having a first shell and a lid mated to the first shell at a first opening, the first opening sized for passage of the battery and the electrolytic capacitor, the implantable housing defining a housing interior,
wherein the battery and the electrolytic capacitor are disposed in the hermetically sealed implantable housing such that a power source form factor defined by a battery exterior of the battery case and a capacitor exterior of the capacitor case substantially matches the housing interior and the plurality of flat battery layers are disposed parallel the planar battery surface of the battery case, with the plurality of flat capacitor layers disposed parallel the planar capacitor surface of the capacitor case.

18. The apparatus of claim 17, wherein the battery and the electrolytic capacitor and are adapted to deliver from about 1.25 joules per amp hour of charge to about 50 joules per amp hour of charge.

19. The apparatus of claim 18, wherein the flat battery includes a battery capacity density of from about 0.23 amp hours per cubic centimeter to about 0.25 amp hours per cubic centimeter.

20. The apparatus of claim 17, wherein the electrolytic capacitor includes an energy density of from about 4.65 joules per cubic centimeter to 6.5 joules per cubic centimeter.

* * * * *